US00PP08607P

United States Patent [19]

VandenBerg

[11] Patent Number: Plant 8,607

[45] Date of Patent: Feb. 22, 1994

[54] CHRYSANTHEMUM PLANT NAMED BARBARA

[75] Inventor: Cornelis P. VandenBerg, Salinas, Calif.

[73] Assignee: Yoder Brothers, Inc., Barberton, Ohio

[21] Appl. No.: 986,531

[22] Filed: Dec. 7, 1992

[51] Int. Cl.[5] ..... A01H 5/00

[52] U.S. Cl. ..... Plt./76

[58] Field of Search .....Plt. 76, 81

*Primary Examiner*—Howard J. Locker

*Attorney, Agent, or Firm*—Foley & Lardner

[57] ABSTRACT

A Chrysanthemum plant named Barbara particularly characterized by its flat capitulum form; decorative capitulum type; dark red-purple ray floret color; diameter across face of capitulum of 31 to 41 mm when fully opened; branching pattern is spreading and prolific, with 8 to 10 breaks after pinch when grown outside under natural daylength in fall flowerings and 4 to 5 breaks when grown in 10 cm pots for spring flowerings; natural season flower date of August 18 to 26 when planting rooted cuttings on June 21 to 25 in Salinas, Calif., and September 28 to 30 when planting rooted cuttings June 15 to June 18 in Hightstown, N.J.; flowering response of 49 to 56 days after rooting in no light/no shade programs in spring in Salinas, Calif.; plant height of 33 to 41 cm when grown in fall under natural daylength with no growth regulators in New Jersey, and 15 to 18 cm when grown in 10 cm pots in spring with no growth regulator applications; and durable, uniform performance.

3 Drawing Sheets

The present invention comprises a new and distinct cultivar of Chrysanthemum, botanically known as *Dendranthema grandiflora*, and referred to by the cultivar name Barbara.

Barbara, identified as 8329 (89-764004), was originated from a cross made by Cornelis P. VandenBerg in a controlled breeding program in Salinas, Calif., in 1989.

The female parent of Barbara was an unnamed seedling identified as 8451 (86-485001) and described as a flat decorative garden mum with a red-bronze ray floret color; flower diameter of 44 to 47 mm; natural season flower date of August 24 to 31 in Salinas, Calif., and of September 27 to Oct. 3 in Hightstown, N.J.; a flowering response in spring of 40 to 49 days; plant height of 23 to 36 cm in fall natural season flowerings in New Jersey, and 23 to 28 cm in spring flowerings in 10 cm pots with 1 application of 2500 ppm B9-SP in Salinas, Calif.

The male parent of Barbara was an unnamed seedling, identified as 8183 (85-05800) and described as dark pink decorative garden mum with many disc florets; flower diameter of 44 mm; natural season flower date of August 30 to September 1 in Salinas, Calif., and September 29 to October 3 in Hightstown, N.J.; and a plant height of 23 to 30 cm in fall natural season flowerings in New Jersey with no growth regulators. The male parent of Barbara was discarded from the program in September 1988.

Barbara was discovered and selected as one flowering plant within the progeny of the stated cross by Cornelis P. VandenBerg in September 1989, in a controlled environment in Salinas, Calif.

The first act of asexual reproduction of Barbara was accomplished when vegetative cuttings were taken from the initial selection in November 1989 in a controlled environment in Salinas, Calif., by technicians working under supervision of Cornelis P. VandenBerg.

Horticultural examination of controlled flowerings of successive plantings has shown that the unique combination of characteristics as herein disclosed for Barbara are firmly fixed and are retained through successive generations of asexual reproduction.

Barbara has not been observed under all possible environmental conditions. The phenotype may vary significantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial practice for small pot spring garden mum production.

The flowering traits have been repeatedly observed and are determined to be basic characteristics of Barbara, which, in combination, distinguish this Chrysanthemum as a new and distinct cultivar:

1. Flat capitulum form.
2. Decorative capitulum type.
3. Dark red-purple ray floret color.
4. Diameter across face of capitulum of 32 to 41 mm when fully opened.
5. Branching pattern is spreading and prolific, with 8 to 10 breaks after pinch when grown outside under natural daylength in fall flowerings and 4 to 5 breaks when grown in 10 cm pots for spring flowerings.
6. Natural season flower date of August 18 to 26 when planting rooted cuttings on June 21 to 25 in Salinas, Calif., and of September 28 to 30 when planting rooted cuttings June 15 to June 18 in Hightstown, N.J.
7. Flowering response of 49 to 56 days after rooting in no light/no shade programs in spring in Salinas, Calif.
8. Plant height of 33 to 41 cm when grown in fall under natural daylength with no growth regulators in New Jersey, and 15 to 18 cm when grown in 10 cm pots in spring with no growth regulator applications.

9. Durable, uniform performance.

The accompanying photographic drawings show typical inflorescence and leaf characteristics of Barbara, with the colors being as nearly true as possible with illustrations of this type.

Sheet 1 is a color photograph of Barbara grown as a pinched spray pot mum with 1 cutting in a 10 cm pot.

Sheet 2 is a black and white photograph of three views of the inflorescence of Barbara.

Sheet 3 is a black and white photograph showing the upper and under sides of the leaves of Barbara at 3 stages of development (mature, intermediate and immature). In sheets 2 and 3 a measuring tape in centimeters has been added. In sheet 1, the foliage color is not accurately depicted. The foliage colors noted below are correct.

Of the commercial cultivars known to the inventor, the most similar in comparison to Barbara is the cultivar identified as Debonair, disclosed in U.S. Plant Pat. No. 5,324. Reference is made to attached Chart A, which compares certain characteristics of Barbara to the same characteristics of Debonair.

Similar traits are capitulum form and type, natural season flower date in Hightstown, N.J. and controlled flowering response in no light/no shade spring flowering programs in Salinas, Calif. The ray floret color of Barbara is a dark red-purple, while the ray floret color of Debonair is purple. Barbara has a much smaller diameter of capitulum, a more prolific branching pattern, an earlier natural season flowering response in Salinas, Calif., and a slightly taller plant height in natural season flowerings when compared with Debonair.

In the following description color references are made to the Royal Horticultural Society Colour Chart. The color values were determined on plant material grown as a pinched garden mum grown outdoors in Salinas, Calif. on Aug. 18, 1992.

Classification:

*Botanical.*—*Dendranthema grandiflora* cv Barbara.

*Commercial.*—Flat decorative spray pot mum and garden mum.

INFLORESCENCE

A. Capitulum:

*Form.*—Flat.

*Type.*—Decorative.

*Diameter across face.*—32 to 41 mm when fully opened.

B. Corolla of ray florets:

*Color (general tonality from a distance of three meters).*—Dark red-purple.

*Color (upper surface).*—72A.

*Color (undersurface).*—Closest to 78B.

*Shape.13* Cross-section of young ray florets concave, longitudinal section of outer ray florets straight.

C. Corolla of disc florets:

*Color (mature).*—9A.

*Color (immature).*—144C. D. Reproductive organs:

*Androecium.*—Present on disc florets only; scant pollen.

*Gynoecium.*—Present on both ray and disc florets.

PLANT

A. General appearance:

*Height.*—33 to 41 cm when grown in fall under natural daylength in New Jersey with no growth regulators, and 15 to 18 cm when grown in 10 cm pots in spring in Salinas, Calif. with no growth regulator applications.

*Branching pattern.*—Spreading and prolific, with 8 to 10 breaks after pinch when grown outside under natural daylength in fall flowerings, and with 4 to 5 breaks when grown in 10 cm pots for spring flowerings.

B. Foliage:

*Color (under surface).*—147A.

*Color (under surface).*—147B.

*Shape.*—See photograph.

CHART A

| CULTIVAR | BARBARA | DEBONAIR |
|---|---|---|
| Ray floret color | Dark red-purple | Purple |
| Capitulum form and type | Flat Decorative | Flat Decorative |
| Diameter across face of capitulum | 32 to 41 mm | 57 to 64 mm |
| Branching pattern | Spreading and prolific | Spreading |
| Nat. season flower date: | | |
| in Salinas, CA | Aug 18 to 26 | Aug 26 to 31 |
| in Hightstown, NJ | Sep 28 to 30 | Sep 24 to 30 |
| Controlled response | 49 to 56 days | 49 to 53 days |
| Plant height: | | |
| in natural season fall | 33 to 41 cm | 30 to 38 cm |
| in 10 cm pots spring | 15 to 18 cm | 15 to 20 cm |

COMPARISONS MADE OF PLANTS GROWN AS UNDER NATURAL SEASON OUTDOOR CONDITIONS IN SALINAS, CALIFORNIA AND IN HIGHTSTOWN, NEW JERSEY AND IN SPRING FLOWERING PROGRAMS IN SALINAS, CALIFORNIA

I claim:

1. A new and distinct Chrysanthemum plant named Barbara, as described and illustrated.

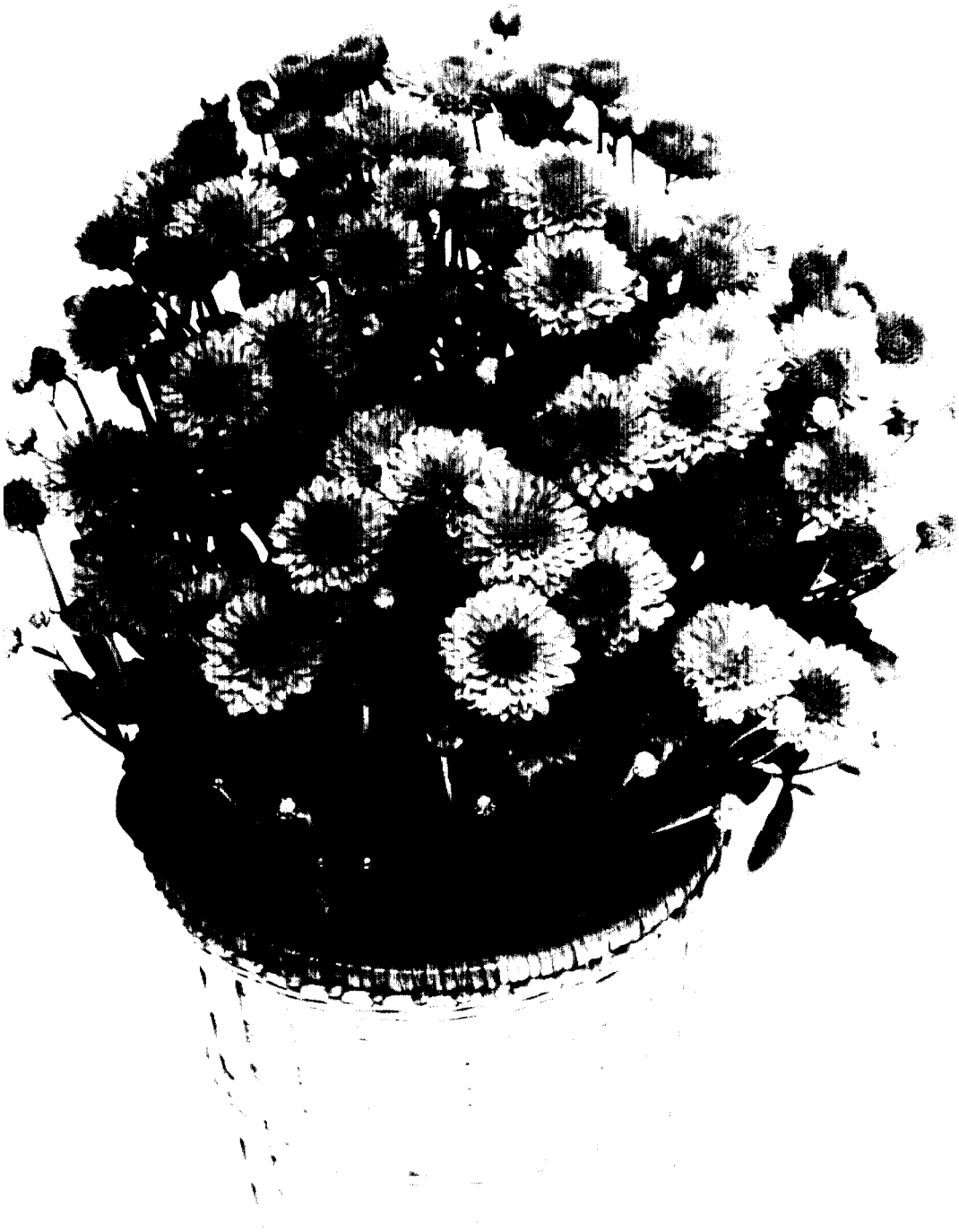

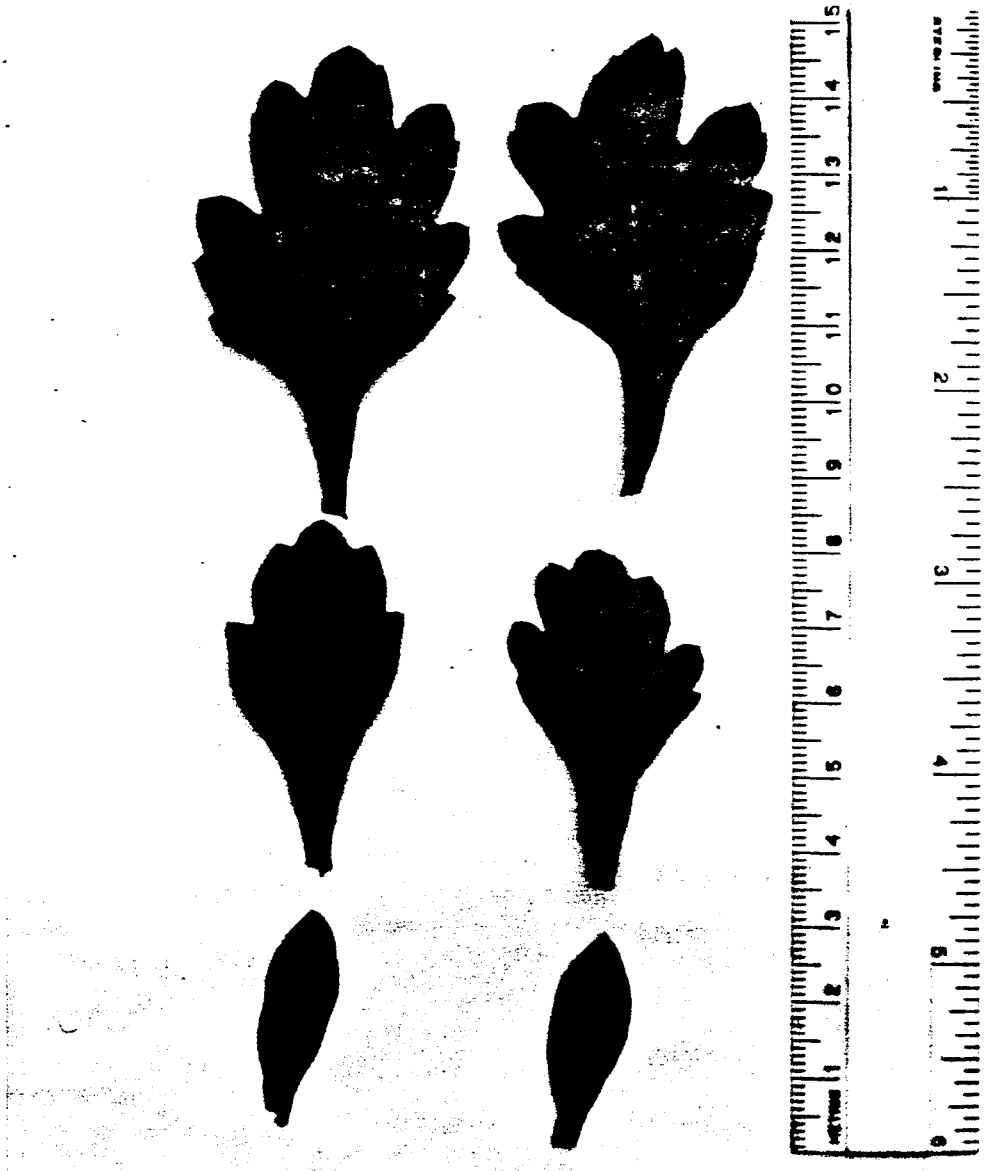

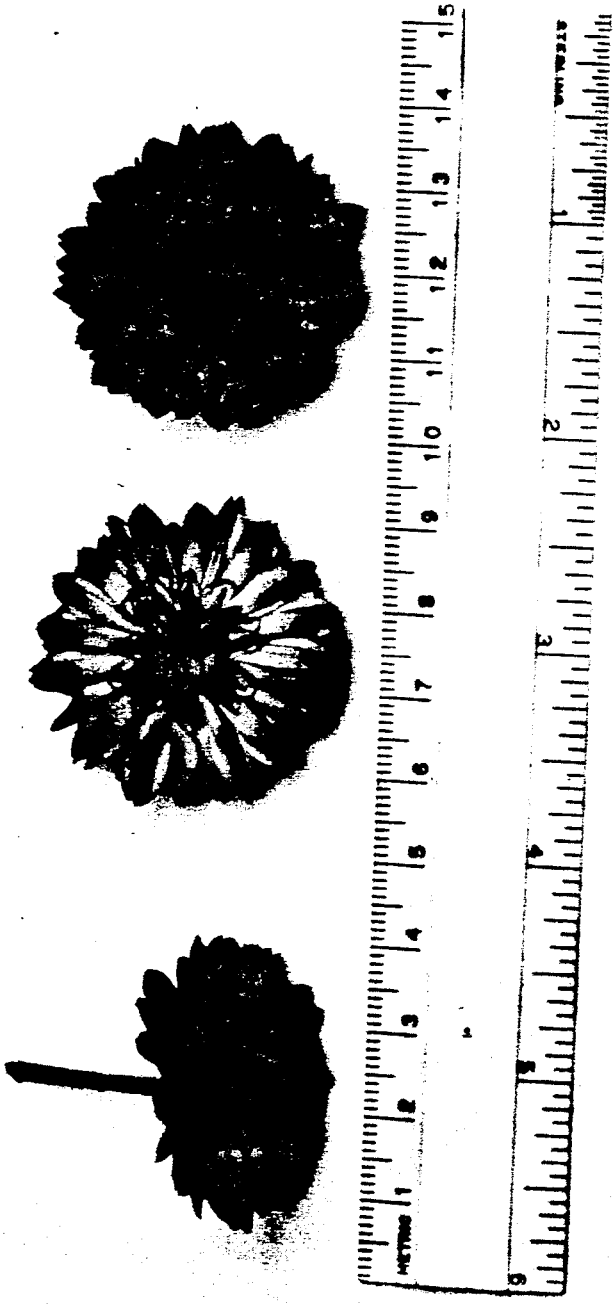

* * * * *